United States Patent
Yasumoto et al.

(10) Patent No.: US 8,538,131 B2
(45) Date of Patent: Sep. 17, 2013

(54) DEFECT INSPECTION APPARATUS AND METHOD OF DEFECT INSPECTION

(75) Inventors: Tamihide Yasumoto, Kawasaki (JP); Naohiro Takahashi, Kawasaki (JP)

(73) Assignee: Fujitsu Semiconductor Limited, Yokohama (JP)

(*) Notice: Subject to any disclaimer, the term of this patent is extended or adjusted under 35 U.S.C. 154(b) by 1023 days.

(21) Appl. No.: 11/511,398

(22) Filed: Aug. 29, 2006

(65) Prior Publication Data
US 2007/0230769 A1 Oct. 4, 2007

(30) Foreign Application Priority Data
Mar. 30, 2006 (JP) ................. 2006-094785

(51) Int. Cl.
*G06K 9/00* (2006.01)
(52) U.S. Cl.
USPC ........................................................... 382/149
(58) Field of Classification Search
USPC ........................................................... 382/149
See application file for complete search history.

(56) References Cited

U.S. PATENT DOCUMENTS

| 6,987,873 | B1* | 1/2006 | Ben-Porath et al. | 382/145 |
|---|---|---|---|---|
| 7,231,079 | B2 | 6/2007 | Okuda et al. | |
| 7,508,973 | B2 | 3/2009 | Okabe et al. | |
| 2002/0051565 | A1* | 5/2002 | Hiroi et al. | 382/149 |
| 2004/0175943 | A1* | 9/2004 | Waksman | 438/689 |
| 2004/0228515 | A1* | 11/2004 | Okabe et al. | 382/145 |

FOREIGN PATENT DOCUMENTS

| JP | 8-94536 A | 4/1996 |
|---|---|---|
| JP | 2002-323458 A | 11/2002 |
| JP | 2005-017159 A | 1/2005 |

OTHER PUBLICATIONS

"Japanese Office Action" mailed by JPO and corresponding to Japanese application No. 2006-094785 on Feb. 22, 2011, with partial English translation.

* cited by examiner

*Primary Examiner* — Brian Q Le
*Assistant Examiner* — Michael Vanchy, Jr.
(74) *Attorney, Agent, or Firm* — Fujitsu Patent Center

(57) ABSTRACT

A first defect classification section uses a pre-inspection test target as the inspected piece, and classifies the defects, based on results of the defect inspection executed a plurality of times by the defect detection system, into first defects detected constantly in each of the plurality of times of inspection, and into second defects detected only in a part of, but not in the residual part of the plurality of times of inspection.

4 Claims, 6 Drawing Sheets

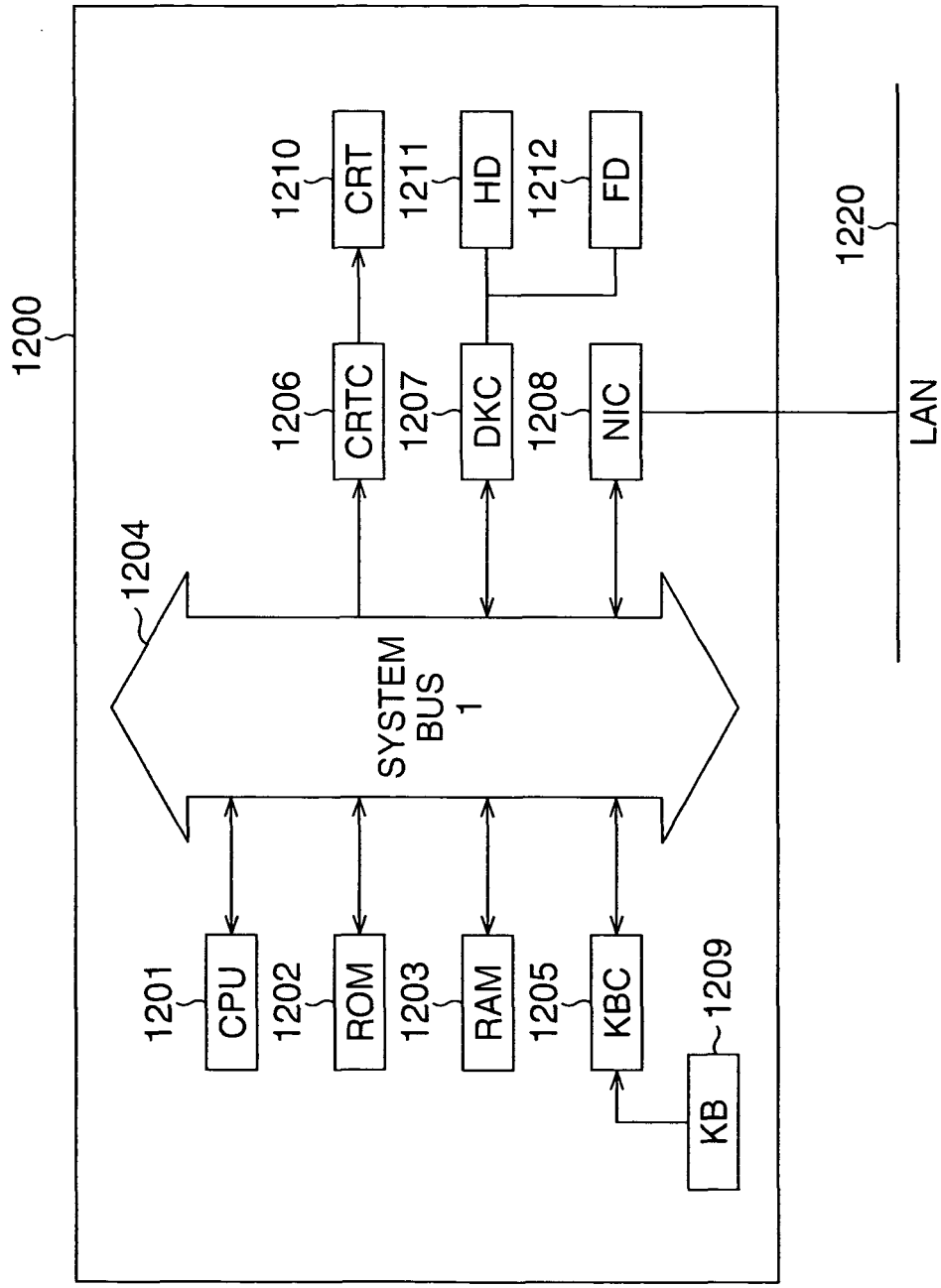

DEFECT INSPECTION APPARATUS AND METHOD OF DEFECT INSPECTION

CROSS-REFERENCE TO RELATED APPLICATIONS

This application is based upon and claims the benefit of priority from the prior Japanese Patent Application No. 2006-094785, filed on Mar. 30, 2006, the entire contents of which are incorporated herein by reference.

BACKGROUND OF THE INVENTION

1. Field of the Invention

The present invention relates to defect inspection apparatus and a method of defect inspection detecting and inspecting defects of an inspected piece.

2. Description of the Related Art

Defect inspection apparatus has been used for the purpose of, for example, observing surface conditions of substrate having micro-structures represented by semiconductor devices formed thereon in an integrated manner, and confirming presence or absence of any defects.

The defect inspection apparatus is provided with a bright-field optical system having an illumination unit irradiating the inspected piece with an illumination beam, and taking an image of regular reflection beam from the inspected piece, or a dark-field optical system having an illumination unit irradiating the inspected piece with an illumination beam, and taking an image of irregular reflection beam from the inspected piece; and inspects defects on the surface of the inspected piece using either or both of the bright-field optical system and the dark-field optical system.

In recent years, a proposal has been made on a defect inspection apparatus capable of executing defect inspection and defect identification in an automated manner, as described in Patent Document 1 below, because visual defect inspection using a defect inspection apparatus casts a large operation load upon an operator and takes a long time for the operation.

Related art is disclosed in Japanese Patent No. 3415943.

In automatic judgment of presence or absence of the defects, the defect inspection apparatus preliminarily sets a predetermined threshold value with respect to intensity of the reflected beam from the inspected piece, and presence or absence of the defects is judged based on a magnitude relation between the threshold value and intensity of the reflected beam. Therefore, intensity of the reflected beam close to the threshold value inevitably destabilizes the judgment of presence or absence of the defects. Even if the threshold value is set in a stable region in which the reflected beam has only a small probability of showing intensity very close to the threshold value, judgment of presence or absence of the defects may be destabilized due to fluctuation in environment of the apparatus, such as set temperature in the apparatus, so that judgment of defects causing reflected beam having an intensity close to the threshold value is still more inevitably destabilized. Another problem resides in that quasi-defects, which do not exist on the real inspected piece, may be observed due to non-uniform color of the surface, and such quasi-defects often show an unstable behavior similarly due to fluctuations in environment of the apparatus.

There has never been proposed a technique of quantitatively understanding the defects (unstable defects) likely to destabilize the judgment of their existence, as being discriminated from the defects (stable defects) allowing stable judgment, so that the technique remains to be expected for further research and development for the future.

SUMMARY OF THE INVENTION

An object of the present invention is to provide a defect inspection apparatus and a method of defect inspection capable of realizing highly-reliable products, by discriminating unstable defects from stable defects, and classifying and identifying both types of defects in a quantitative and accurate manner relying upon only a relatively simple configuration, and further by understanding tendency of occurrence of the unstable defects and managing it as a standard index for routine inspection of an inspected piece.

A defect inspection apparatus of the present invention has a defect detection system detecting defects of an inspected piece; and a first defect classification unit classifying the defects, based on results of a plurality of times of defect inspection executed by the defect detection system using a pre-inspection test target as the inspected piece, into first defects detected constantly in each of the plurality of times of inspection, and into second defects detected only in a part of, but not in the residual part of the plurality of times of inspection.

A method of defect inspection of the present invention has a step of executing, while using a pre-inspection test target as an inspected piece, defect inspection of the test target a plurality number of times; and a step of executing a first classification classifying the defects, based on results of the defect inspection of the test target, into first defects detected constantly in each of the plurality of times of inspection, and into second defects detected only in a part of, but not in the residual part of the plurality of times of inspection.

BRIEF DESCRIPTION OF THE DRAWINGS

FIG. 7 is a schematic drawing showing an internal configuration of a personal user terminal device.

DETAILED DESCRIPTION OF THE PREFERRED EMBODIMENTS

Basic Concept of the Present Invention

Figure 1:
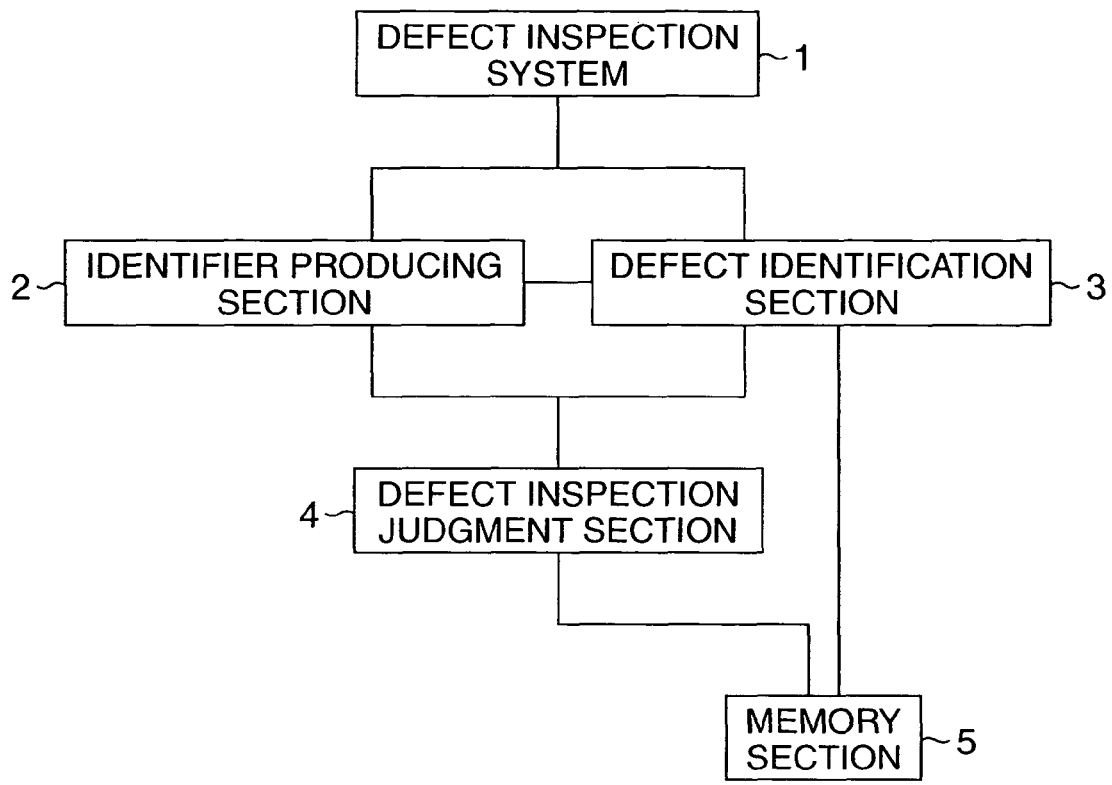
FIG. 1 is a block diagram showing a schematic configuration of a defect inspection apparatus according to one embodiment.

As described in the above, the unstable defects are supposed to be ascribable mainly to setting of threshold value of the defect detection system (having a bright-field optical system, a dark-field optical system, and a defect judgment section) or to environments of the apparatus. The present inventors considered that, by preliminarily identifying unstable defects using the defect detection system prior to defect inspection (actual inspection) of an inspected piece destined for the final product, results of the identification are applicable to the actual inspection.

In the present invention, in order to discriminate the unstable defects from the stable defects and to quantitatively understand the both, an index for identifying the stable defects and the unstable defects is preliminarily prepared, using a pre-inspection test target as the inspected piece, prior to the actual inspection.

In further detail, the defect inspection of the inspected piece to be tested, is executed a plurality of times using the defect detection system. It is our first thought to use a test-dedicated inspected piece as the inspected piece to be tested, but it is also allowable to use an inspected piece arbitrarily selected from those destined for the final products later subjected to the actual inspection.

The defects are then classified, based on results of the defect inspection repeated a plurality of times, into first defects detected constantly in each of the plurality of times of inspection, and into second defects detected only in a part of, but not in the residual part of the plurality of times of inspection. Information of thus-classified first and second defects (coordinate information of positions of defects, for example) is used as an index for identifying the stable defects and the unstable defects. Population of the first defects is counted while masking the second defects using a predetermined software, and a total count is used as a judgment base value.

Next, using the above-described defect detection system, the inspected piece destined for the final product, that is, a target for the actual inspection, is subjected to defect detection. Results of the detection are then collated with information on the second defects, and the defects are classified while assuming those agreed with the second defects as unstable defects, and assuming those disagreed with the second defects as stable defects. Based on the classification, a total count of the unstable defects and a total count of the stable defects are respectively counted. The total count of the stable defects is then collated with the above-described judgment base value, and quality of the defect inspection of the inspected piece, which is a target for actual inspection, is judged based on a magnitude relation of the total count of the stable defects with the judgment base value. On the other hand, the total count of the unstable defect is fed back as expressing a tendency of occurrence of the unstable defects in the defect detection system, and subjected to management of the apparatus.

As has been described in the above, according to the present invention, the unstable defects can be discriminated from the stable defects relying upon only a relatively simple configuration, and both types of defects can be classified and identified in a quantitative and accurate manner. Moreover, it is also made possible to understand tendency of occurrence of the unstable defects, and to manage the tendency as a standard index for routine inspection of the inspected piece.

Preferred Embodiments Applied with the Present Invention

Paragraphs below will detail preferred embodiments applied with the present invention, referring to the attached drawings.

FIG. 1 is a block diagram showing a schematic configuration of a defect inspection apparatus according to one embodiment.

The defect inspection apparatus is configured as having a defect inspection system 1 inspecting defects on a inspected piece, which is for example a semiconductor substrate having semiconductor devices formed thereon; an identifier producing section 2 producing, using a pre-inspection test target as an inspected piece, an identifier discriminating the stable defects from the unstable defects; a defect identification section 3 quantitatively identifying the defects detected in an actual inspection as the stable defects or the unstable defects; a defect inspection judgment section 4 making various judgments based on information on thus-identified stable defects or unstable defects; and a memory section 5 storing information on results of judgment and so forth obtained by the defect inspection judgment section 4. Individual operations of the defect inspection system 1, the identifier producing section 2, the defect identification section 3, and the defect inspection judgment section 4 are generally controlled by an unillustrated control section.

Figure 2:
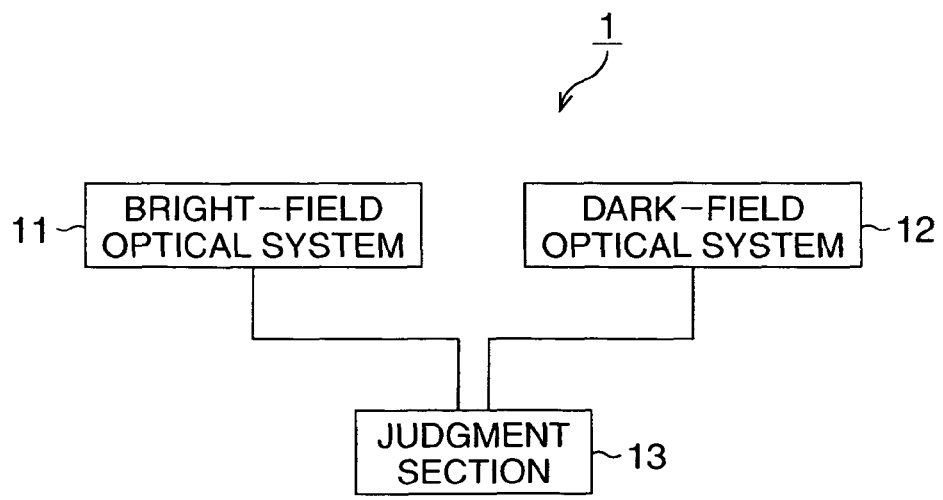
FIG. 2 is a block diagram showing a schematic configuration of a defect inspection system which is a constituent of the defect inspection apparatus according to the embodiment.

The defect inspection system 1 is configured as having, as shown in FIG. 2, a bright-field optical system 11 or a dark-field optical system 12, and a judgment section 13.

The bright-field optical system 11 has a light source irradiating the inspected piece with an illumination beam, which is typically laser beam or beam from a lamp (UV lamp, halogen lamp, and so forth), aimed at taking an image of regular reflection beam of the illumination beam from the inspected piece.

The dark-field optical system 12 has a light source irradiating the inspected piece with an illumination beam, which is typically laser beam, aimed at taking an image of irregular reflection beam (scattered light) of the illumination beam from the inspected piece.

The judgment section 13 judges presence or absence of any defects, based on the images taken respectively by the bright-field optical system 11 and the dark-field optical system 12, and on the basis of a predetermined set threshold value.

In this embodiment, defects on a semiconductor substrate 10 are sequentially inspected by illuminating the surface of the semiconductor substrate 10 by the bright-field optical system 11 and the dark-field optical system 12, and the defect judgment is made by the judgment section 13.

Figure 3A:
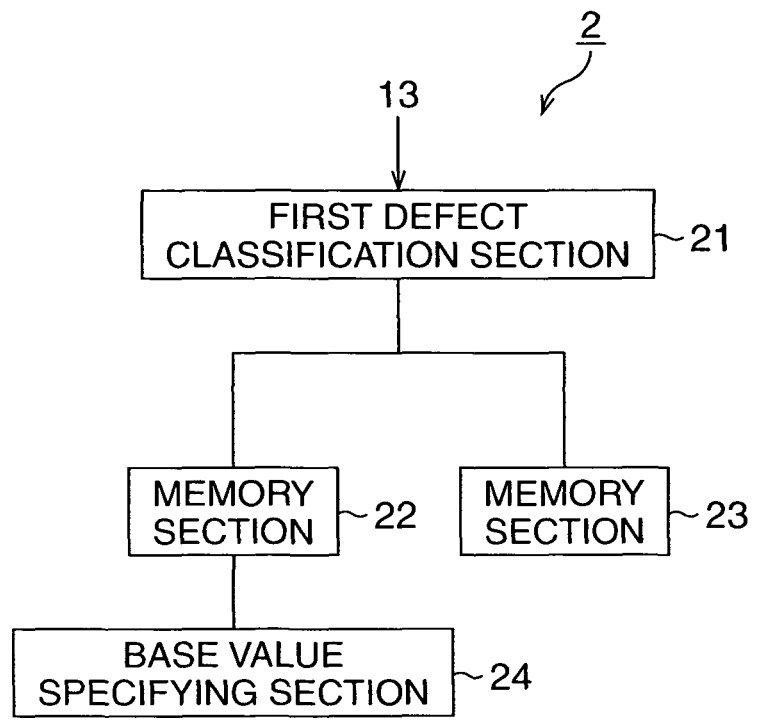
FIGS. 3A and 3B are block diagrams showing schematic configurations of an identifier producing section which is a constituent of the defect inspection apparatus according to the embodiment.

The identifier producing section 2 is configured as having, as shown in FIG. 3A, a first defect classification section 21, memory sections 22, 23, and a base value specifying section 24.

The first defect classification section 21 uses a pre-inspection test target as the inspected piece, and classifies the defects based on results of the defect inspection repeated a plurality of times by the defect detection system, into first defects detected constantly in each of the plurality of times of inspection, and into second defects detected only in a part of, but not in the residual part of the plurality of times of inspection.

Figure 5A:
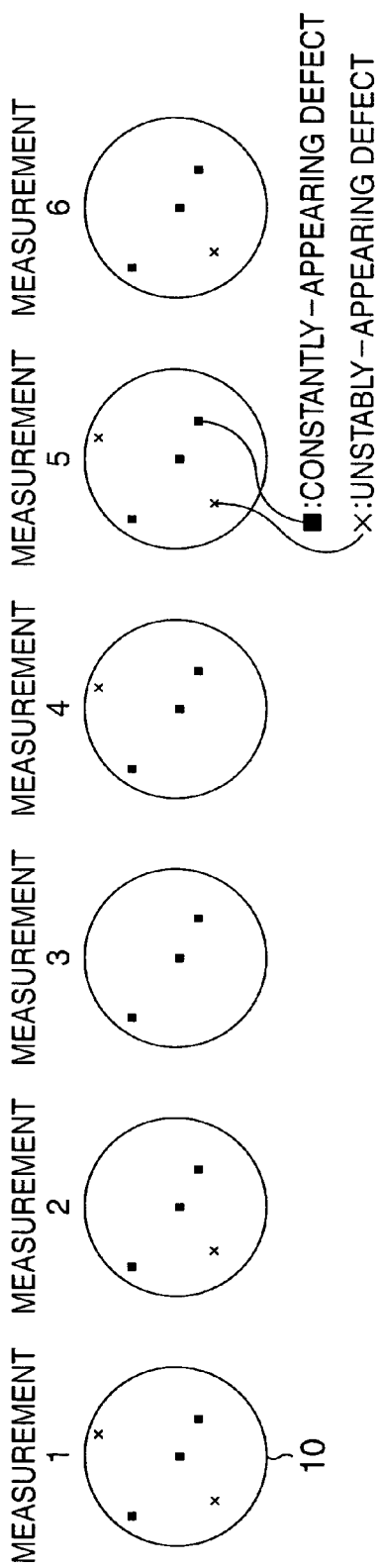
FIGS. 5A and 5B are schematic plan views showing specific examples of the method of defect identification by a first defect classification section.

For an exemplary case shown in FIG. 5A where the defect inspection is repeated six times, the first defects are those detected in all of six times of defect inspection at the same places on the semiconductor substrate 10 (indicated by ■ in the drawing), and the second defects are those detected only a part of six times of inspection at the same places (indicated by x in the drawing).

Figure 3B:
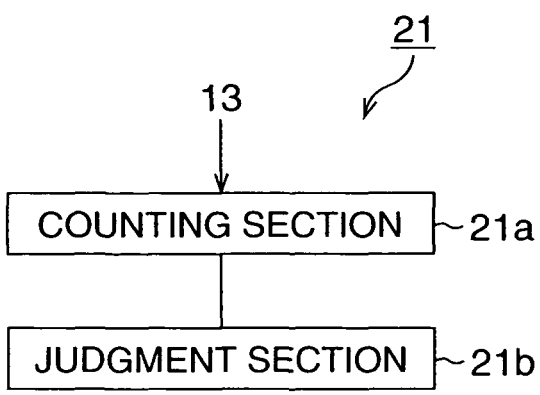

More specifically, the first defect classification section 21 is configured as having, as shown in FIG. 3B, a counting section 21a counting the number of times of detection, out of the plurality of times, for every defect detected by the defect detection system using a test target inspected piece; and a judgment section 21b judging whether the number of times of detection of the defects at the same positions on the coordinate, as a result of the counting by the counting section 21a, is less than the above-described plurality of times (for example, five times or less for a plurality of times of six) or not. If the number of times of detection is judged by the judgment section 21b as being equal to the above-described plurality of times, the detected defects herein are classified into the first defects. On the other hand, if the number of times of detection is less than the plurality of times, the detected defects herein are classified into the second defect.

The memory section 22 registers and stores information on the first defects. The memory section 23 registers and stores information on the second defects.

Figure 5B:
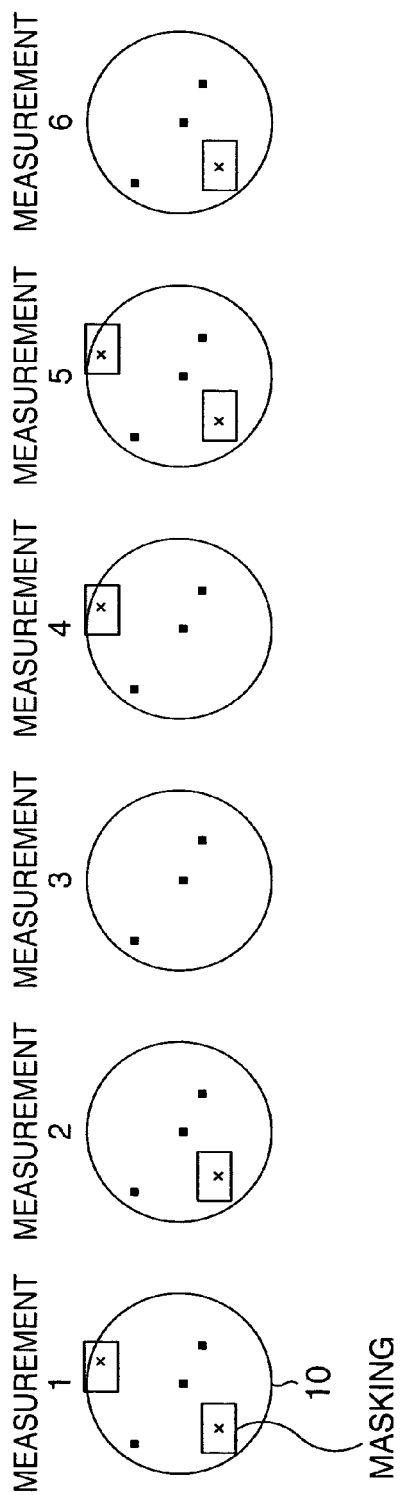

The base value specifying section 24 calculates a total count of the first defects based on information on the first defects stored in the memory section 22, and specifies the total count of the first defects as the judgment base value. For example, as shown in FIG. 5B, the second defects (indicated by x in the drawing) on the semiconductor substrate 10 are masked using a predetermined software, the number of the first defects is counted in this state, and the total count is specified as the judgment base value. The judgment base value in the exemplary case shown in FIGS. 5A and 5B appears to be three.

Figure 4:
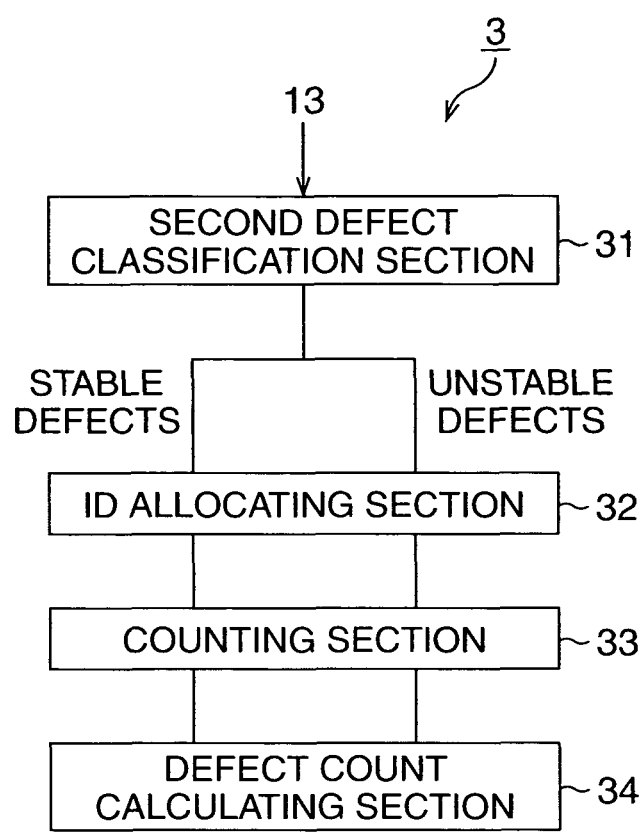
FIG. 4 is a block diagram showing a schematic configuration of a defect identification section which is a constituent of the defect inspection apparatus according to the embodiment.

The defect identification section 3 is configured, as shown in FIG. 4, as having a second defect classification section 31, an ID allocating section 32, a counting section 33, and a defect count calculating section.

The second defect classification section 31 collates defects of the inspected piece, which is a target for the actual inspection, detected by the defect detection system 1 one by one with information on the second defects recognized on the test target, and classifies the defects while assuming those agreed with the second defects as unstable defects, and assuming those disagreed with the second defects as stable defects.

The ID allocating section 32 allocates an ID to information of each defect classified either into the unstable defect or stable defect.

The counting section 33 respectively counts up, for each defect, the unstable defects and the stable defects based on the allocated IDs.

The defect count calculating section 34 respectively calculates a total count of the unstable defects and a total count of the stable defects. Information on the total count of the unstable defects calculated by the defect count calculating section 34 is stored in the memory section 5.

The defect inspection judgment section 4 collates the total count of the stable defects with the above-described judgment base value, and judges quality of the defect inspection of the inspected piece, which is a target for the actual inspection, based on a magnitude relation between the total count of the stable defects and the judgment base value. In the exemplary case shown in FIGS. 5A and 5B, the result of the defect inspection of the inspected piece is judged as being acceptable if the total count of the stable defects is not larger than three, which is the judgment base value. On the other hand, the result of the defect inspection of the inspected piece is judged as being unacceptable if the total count of the stable defect is 4 or larger. In case of unacceptable judgment, the result of the defect inspection is subjected to investigations for finding causes and future measures. On the other hand, the total count of the unstable defects calculated by the defect count calculating section 34 is fed back as expressing tendency of occurrence of the unstable defects in the defect detection system, and subjected to management of the apparatus. Information on the results judged by the defect inspection judgment section 4 is stored in the memory section 5.

The defect inspection apparatus of this embodiment has been explained as being configured as incorporating the defect detection system, whereas it is also allowable to configure the defect detection system as an independent defect inspection apparatus or as the one available elsewhere, and a system composed of the other constituents (identifier producing section 2, defect identification section 3, and defect inspection judgment section 4) is configured as an external defect identification apparatus attached to the defect inspection apparatus, so as to configure a defect inspection system using the defect inspection apparatus and the defect identification apparatus.

Paragraphs below will explain a method of defect inspection using the above-described defect inspection apparatus.

Figure 6:
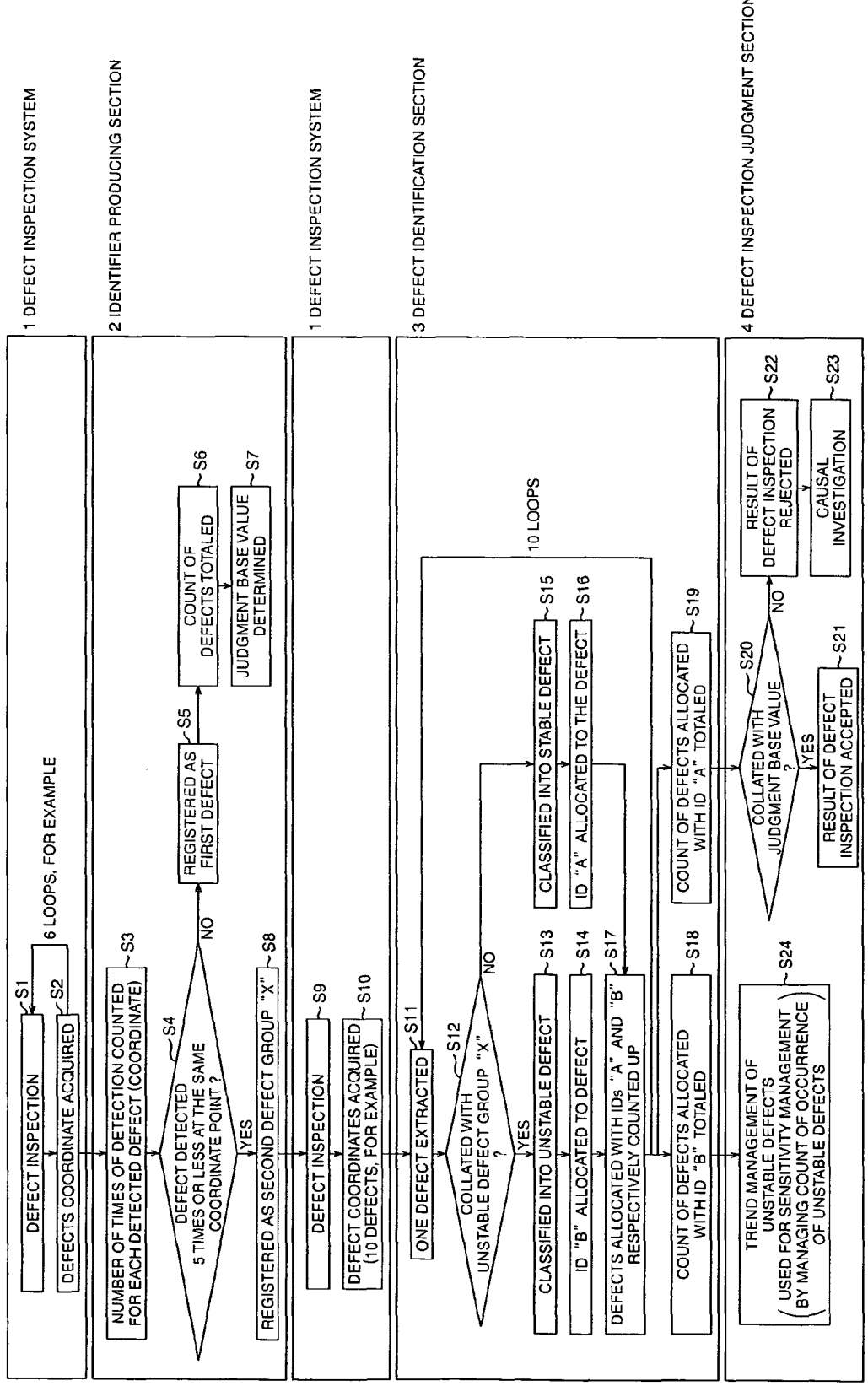
FIG. 6 is a flow chart sequentially showing process steps of a method of defect inspection according to the embodiment.

FIG. 6 is a flow chart sequentially showing process steps in a method of defect inspection according to the embodiment.

First, the defect inspection is executed by the bright-field optical system 11 or the dark-field optical system 12 of the defect inspection system 1, using a pre-inspection test target as the inspected piece (step S1). It is our first thought to use a test-dedicated inspected piece, which is typically a test-dedicated semiconductor substrate, as the inspected piece to be tested, but it is also allowable to use an inspected piece arbitrarily selected from those destined for the final products later subjected to the actual inspection.

Next, positions on the coordinate of the individual defects recognized by the defect inspection are acquired by the judgment section 13 of the defect inspection system 1 (step S2).

In this embodiment, steps S1, S2 are executed a plurality of times (6 times in the illustrated example, and throughout the paragraphs below) using the same test-dedicated inspected piece.

Next, the number of times of detection out of six times of inspection is counted by the counting section 21a of the first defect classification section 21, for every defect detected by the defect detection system using the inspected piece (step S3).

Next, whether the number of times the defect was detected at the same position on the coordinate, counted by the counting section 21b, is not larger than five or not is judged by the judgment section 21b of the first defect classification section 21 (step S4).

If the number of times the defect was detected is judged as being six in step 4, the defect is classified into the first defect, and information on the result is registered and stored in the memory section 22 (step S5). A total count of the first defect is then calculated by the base value specifying section 24, based on the information on the first defects stored in the memory section 22 (step S6). The total count of the first defects is specified as the judgment base value (step S7).

On the other hand, if the number of times the defect was detected at the same position on the coordinate, counted by the counting section 21a, is judged as being five or less, the defect is classified into the second defect, typically registered as a second defect group "X", and stored in the memory section 23 (step S8).

Next, the inspected piece, which is a target for the actual inspection and is typically a semiconductor substrate, is subjected to defect inspection by the bright-field optical system or the dark-field optical system 12 of the defect inspection system (step S9).

Next, for each of the defects recognized as a result of the defect inspection (10 defects in the illustrated example, and throughout the paragraphs below), a position on the coordinate is acquired by the judgment section 13 of the defect inspection system 1 (step S10).

Next, one defect out of the defects of the inspected piece, which is a target for actual inspection, detected by the defect detection system 1 is extracted (step S11). The extracted defect is collated with information on the second defect stored as a second defect group "X" in the memory section 23 (step S12). Those defects agreed with the second defect as a result of the collation are assumed as the unstable defects, and classified thereinto (step S13). Information on the defects classified into the unstable defects is allocated with an ID "B" by the ID allocating section 32 (step S14). On the other hand, the defects disagreed with the second defect are assumed as the stable defects, and classified thereinto (step S15). Information on the defects classified into the stable defects is allocated with an ID "A" by the ID allocating section 32 (step S16).

Next, based on thus-allocated IDs "B" and "A", the unstable defects and the stable defect are respectively counted up (step S17).

In this embodiment, steps S11 to S17 are executed for each of ten defects recognized by the defect inspection system 1 (that is, repeated 10 times), and a total count of the unstable defects and a total count of the stable defects are respectively calculated by the defect count calculating section 34 (steps S18, S19).

Next, the total count of the stable defects calculated by the defect count calculating section 34 is collated with the above-described judgment base value (step S20). If the total count of the stable defects was found, by the collation, to be not larger than the judgment base value, the result of the defect inspection of the inspected piece is judged as acceptable (step S21). On the other hand, if the total count of the stable defects was found to be larger than the judgment base value, (judgment base value +1 or more), the result of the defect inspection of the inspected piece is judged as unacceptable (step S22). In case of the unacceptable judgment, the result of the defect inspection is subjected to investigations for finding causes and future measures (step S23). On the other hand, the total count of the unstable defects calculated by the defect count calculating section 34 is subjected to management of the apparatus, as expressing tendency of occurrence of the unstable defects in the defect detection system (step S24).

As has been described in the above, according to the present invention, the unstable defects can be discriminated from the stable defects relying upon only a relatively simple configuration, and both types of defects can be classified and identified in a quantitative and accurate manner. Moreover, it is also made possible to understand tendency of occurrence of the unstable defects, and to manage the tendency as a standard index for routine inspection of the inspected piece.

Functions of the individual constituents composing the defect inspection apparatus of this embodiment (the judgment section 13 of the defect inspection system 1; the first defect classification section 21 and the base value specifying section 24 of the identifier producing section 2; individual constituents of the defect identification section 3; the defect inspection judgment section 4; and so forth) can be realized by execution of a program stored in a RAM or a ROM of a computer. Similarly, the individual steps (steps S1 to S24 in FIG. 6, and so forth) of the method of defect inspection can be realized by execution of the program stored in the RAM or the ROM of the computer. Also the program and a computer-readable storage media having the program stored therein are within the scope of the present invention.

More specifically, the program is supplied to the computer, in a form of being recorded in one of recording media such as CD-ROM, or through various transmission media. The recording media to which the program is recordable, other than CD-ROM, include flexible disc, hard disc, magnetic tape, magneto-optical disc, non-volatile memory card and so forth. On the other hand, as the transmission media of the program 1, available is a communication medium in a computer network system capable of supplying program information by carrier-wave-assisted transmission. The computer network herein includes LAN, WAN such as the Internet, radio communication network and so forth, and the communication media include and wired circuit such as optical fiber circuit, wireless circuit and so forth.

The program included in the present invention is not only the one such as realizing the functions described in the above embodiment, by being executed by the computer. For example, the program is included in the present invention also for the case where the program can realize the functions described in the above embodiment in cooperation with an OS (operating system) or any other application software running on the computer. The program is included in the present invention still also for the case where the all of, or a part of processing by the supplied program is executed on a function-expansion board or a function-expansion unit of the computer.

FIG. 7 is a schematic drawing showing an exemplary internal configuration of a personal user terminal device. In FIG. 7, reference numeral 1200 represents a personal computer (PC) equipped with a CPU 1201. The PC 1200 executes a device control software stored in a ROM 1202 or a hard disc (HD) 1211, or supplied from a flexible disc drive (FD) 1212. The PC 1200 generally controls the individual devices connected to a system bus 1204.

The procedures of steps S1 to S24 shown in FIG. 6, for example, are realized by the program stored in the CPU 1201, the ROM 1202 or the hard disc (HD) 1211 of the PC 1200.

Reference numeral 1203 represents a RAM which functions as a main memory, a work area and so forth of the CPU 1201. Reference numeral 1205 represents a keyboard controller (KBC) controlling command input through a keyboard (KB) 1209 or any other unillustrated devices.

Reference numeral 1206 represents a CRT controller (CRTC) controlling display on a CRT display (CRT) 1210. Reference numeral 1207 represents a disc controller (DKC). The DKC 1207 controls access to the hard disc (HD) 1211 and the flexible disc (FD) 1212 storing a boot program, a plurality of applications, editor, user file, network management program and so forth. The boot program herein means a start program initiating execution (operation) of hardware and software of the personal computer.

Reference numeral 1208 represents a network interface card (NIC), assisting bidirectional data transmission through a LAN 1220 with a network printer, other network devices, or other PCs.

The present invention is successful in realizing highly-reliable products by discriminating unstable defects from stable defects relying upon only a relatively simple configuration, and by classifying and identifying both types of defects in a quantitative and accurate manner, and further by understanding tendency of occurrence of the unstable defects and managing it as a standard index for routine inspection of an inspected piece.

What is claimed is:

1. A method of defect inspection comprising:
   executing defect inspection of a first inspected piece a plurality of times using a defect inspection apparatus;
   executing a first classification classifying the defects, based on results of said defect inspection of said first inspected piece, into first defects detected constantly in each of said plurality of times of inspection, and into second defects detected only in a part of, but not in the residual part of said plurality of times of inspection;

executing a second classification collating defects of a second inspected piece detected by said defect detection system, with information on said second defects recognized on said first inspected piece, and classifying said defects while assuming those agreed with said second defects as unstable defects, and assuming those disagreed with said second defects as stable defects;

calculating a total count of said first defects, based on said first classification, and specifying the total count of said first defects as a judgment base value, in which said second defects are masked, the number of said first defects is counted in this state, and the total count is used as the judgment base value;

respectively calculating a total count of said unstable defects and a total count of said stable defects, based on said second classification;

collating the total count of said stable defects recognized on said second inspected piece with said judgment base value determined from said first inspected piece, and judging the result of the defect inspection of said second inspected piece as being unacceptable if said total count of the stable defects is larger than said judgment base value; and feeding back said total count of the unstable defects calculated by said calculating as expressing tendency of occurrence of the unstable defects, which is ascribable to setting of threshold value of the defect detection system and to environments of the apparatus, to said defect inspection apparatus, and managing the tendency as a standard index in the defect detection system.

2. The method of defect inspection according to claim 1, further comprising:

storing information on said second defects classified by said second classification.

3. The method of defect inspection according to claim 1, wherein the defects classified into said stable defects are allocated with a first ID, and the defects classified into said unstable defects are allocated with a second ID; and based on the first and second IDs, the total count of said stable defects and the total count of said unstable defects are respectively calculated.

4. The method of defect inspection according to claim 1, wherein said executing defect inspection of the first inspected piece a plurality of times is performed under a constant defect inspection sensitivity of the defect inspection apparatus.

* * * * *